United States Patent [19]
Andreiko et al.

[11] Patent Number: 5,395,238
[45] Date of Patent: Mar. 7, 1995

[54] METHOD OF FORMING ORTHODONTIC BRACE

[75] Inventors: Craig A. Andreiko, Alta Loma; Mark A. Payne, Whittier, both of Calif.

[73] Assignee: Ormco Corporation, Glendora, Calif.

[21] Appl. No.: 141,376

[22] Filed: Oct. 22, 1993

Related U.S. Application Data

[63] Continuation of Ser. No. 775,589, Oct. 15, 1991, abandoned, and a continuation-in-part of Ser. No. 467,162, Jan. 19, 1990, Pat. No. 5,139,419.

[51] Int. Cl.$^6$ ............................................. A61C 3/00
[52] U.S. Cl. ...................................................... 433/24
[58] Field of Search ........................................ 433/24

[56] References Cited

U.S. PATENT DOCUMENTS

| | | | |
|---|---|---|---|
| 2,467,432 | 4/1949 | Kesling | 433/6 |
| 3,477,128 | 11/1969 | Andrews | 433/24 |
| 3,660,900 | 5/1972 | Andrews | 433/24 |
| 3,686,762 | 8/1972 | Sutter | 433/24 |
| 3,738,005 | 6/1973 | Cohen et al. | 433/24 |
| 3,821,469 | 6/1974 | Whetstone et al. | 178/18 |
| 3,906,634 | 9/1975 | Aspel | 433/24 |
| 3,949,478 | 4/1976 | Schinhammer | 433/24 |
| 4,014,096 | 3/1977 | Dellinger | 433/24 |
| 4,160,322 | 7/1979 | Frazier | 433/24 |
| 4,165,561 | 8/1979 | Miller et al. | 433/24 |
| 4,183,141 | 1/1980 | Dellinger et al. | 433/24 |
| 4,324,546 | 4/1982 | Heitlinger et al. | 433/213 |
| 4,360,341 | 11/1982 | Dellinger | 433/24 |
| 4,611,288 | 9/1986 | Duret et al. | 433/213 |
| 4,663,720 | 5/1987 | Duret et al. | 433/214 |
| 4,742,464 | 5/1988 | Duret et al. | 433/214 |
| 4,837,732 | 6/1989 | Brandestini et al. | 433/223 |
| 4,850,864 | 7/1989 | Diamond | 433/24 |
| 5,011,405 | 4/1991 | Lemchen | 433/24 |
| 5,027,281 | 6/1991 | Rekow et al. | 364/474.24 |
| 5,100,316 | 3/1992 | Wildman | 433/24 |

FOREIGN PATENT DOCUMENTS 02218  5/1989  WIPO .

OTHER PUBLICATIONS

Leinfelder, K. F., Barry, P. Isenberg, Essig, Milton, E., "A new method for generating ceramic restorations: a CAD-CAM system", Journal American Dental Assoc., vol. 118, Jun. 1989, pp. 703-707.

Rekow, Dianne, "Computer-aided design and manufacturing in dentistry; A review of the state of the art", Journal of Prosthetic Denistry, vol. 58, Oct., 1967, pp. 512-516.

*Primary Examiner*—Cary E. O'Connor
*Attorney, Agent, or Firm*—Wood, Herron & Evans

[57] ABSTRACT

Contours of a patient's teeth are digitally determined from individual teeth of a model of the patient's mouth provided by an orthodontist, preferably by scanning individual teeth in a lingual-facial plane on the model with a mechanical probe. Tooth prominence parameters including tooth-gum intersections, mesial cusp tips or lingual and facial incisal edge points, and groove/ridge locations are selected on the contours. Tooth long axes are derived therefrom in the contour plane through the gum intersection and incisal edge/cusp tip midpoints and the contours are oriented to in the plane to predetermined inclination angles. From these, calculations are made to locate brackets on the contours and determine geometry of slots to cut in the brackets for disposition of a curved archwire in a horizontal plane so as to incline the axes and position the tooth parameters as desired relative to each other when the brace is installed as calculated, using a mold of the brace and model and/or written instructions provided with the brace, and without the need for the orthodontist to bend the archwire. The bite resulting preferably places lower buccal cusps in upper marginal ridges on bicuspids and molars.

33 Claims, 8 Drawing Sheets

UPPER MOLAR

LOWER BICUSPID

UPPER CUSPID, LATERAL OR CENTRAL

LOWER CUSPID, LATERAL OR CENTRAL

METHOD OF FORMING ORTHODONTIC BRACE

This application is a continuation-in-part of U.S. patent application Ser. No. 07/467,162, filed Jan. 19, 1990, now U.S. Pat. No. 5,139,419; and a continuation of U.S. patent application Ser. No. 07/775,589, filed Oct. 15, 1991, now abandoned.

This invention relates to a method of forming an orthodontic brace from a plurality of brackets and an unbent arch wire such that the proper forces are applied by the brace to a patient's teeth to move the patient's teeth into a desired configuration. The invention further relates to a method of processing the parameters individual to a patient's teeth to form slots in brackets and position the brackets on the patient's teeth such that an arch wire disposed in the slots in the brackets will have a planar configuration in an elevational view and a progressively curved configuration in a planar view.

BACKGROUND OF THE INVENTION

When the teeth in a patient's mouth are displaced from an even or uniform disposition, such displacements tend to produce problems over an extended period of time. For example, such displacements may produce problems in the patient's gums. These problems may cause the retention of teeth by the patient's gums to become weakened so that the teeth become loose in the patient's mouth. The problem may become so aggravated that the teeth may eventually have to be removed from the patient's mouth.

To prevent the conditions in a patient's mouth from deteriorating, orthodontists often attempt to reset the positions of the teeth in the patient's mouth. The orthodontists do this by attaching braces to the patient's teeth and by gradually adjusting the forces applied by the braces to the teeth. These forces act against the teeth in the patient's mouth to move the teeth gradually toward the positions desired by the orthodontist.

The braces are generally formed by brackets and an arch wire supported in a slot or groove in each of the brackets. Each bracket is adhered to an individual tooth by a pad forming a part of the bracket. The arch wire extends between the brackets on adjacent teeth and applies a force to the teeth to move the teeth toward the positions determined by the patient's orthodontist. Until now, the grooves on the different brackets have been substantially uniform. Because of this, the forces of the arch wire on the teeth have had to be adjusted by bending or otherwise distorting the wires.

The techniques discussed in the previous paragraph have had some beneficial effect. However, they are expensive and imperfect. One reason is that they require a considerable amount of work by the orthodontist to adjust progressively the forces applied against the teeth. Another reason is that the bending and distortion of the arch wire to adjust the forces on the different teeth have been empirical or intuitive on the part of the orthodontist and have been based in large part upon the experience of the orthodontist. As will be appreciated, even an experienced orthodontist is not able to bend or twist an arch wire precisely so that the proper force will be produced on the brackets attached to the individual teeth.

It has been appreciated in the art that it would be desirable to construct the brackets so that the arch wire is planar in an elevational view and is progressively curved in a plan view even after attachment to the brackets and after the disposition in the patient's mouth of the brace formed by the brackets and the arch wire. For example, such a brace has been proposed in U.S. Pat. No. 3,477,128 issued to Lawrence F. Andrews on Nov. 11, 1969 and U.S. Pat. No. 3,660,900 issued to Lawrence F. Andrews on May 9, 1972.

The proposals made by Andrews are based upon measurements made in a few skulls. They are not made on an individual basis for each patient. Furthermore, the proposals made by Andrews involve only a limited number of parameters. These parameters are mostly confined to individual characteristics of the grooves in the brackets. As will be appreciated, the proposals made by Andrews are quite crude and would not be sufficient to provide, for the individual parameters represented by the unique configuration and disposition of the teeth in each patient's mouth, a brace in which the arch wire is planar in an elevational view and is progressively curved in a plan view. U.S. Pat. No. 5,011,405 issued on Apr. 30, 1991, to Marc S. Lemchen for a "Method of Determining Orthodontic Bracket Placement" and assigned of record to Dolphin Imaging Systems is also pertinent with respect to methods of positioning brackets on an arch wire to dispose a patient's teeth in optimal positions in the patient's mouth.

The Andrews patents are now twenty years old (in one case), or almost twenty years old (in the other case). In that period of time, no one has been able to advance the state of the art beyond the crude state proposed by Andrews. As a practical matter, no one has been able to dispose an arch wire on the slots in brackets on a patient's teeth so that the arch wire is planar in an elevational view and is progressively curved in a planar view and so that the arch wire will adjust the positioning of the patient's teeth to a model relationship determined by the orthodontist. This is true even though a considerable effort has been made, and a significant amount of money has been expended, to advance the state of the art in the last twenty years.

In co-pending application Ser. No. 07/467,162 filed by Craig A. Andreiko and Terry L. Sterrett on Jan. 19, 1990, for a "Method of Forming Orthodontic Brace and Orthodontic Brace Formed By Such Method", now U.S. Pat. No. 5,139,419 is disclosed for forming slots or grooves in brackets with individual parameters, and for disposing the brackets at individual positions on a patient's teeth, to obtain a disposition of an arch wire in the slots in the brackets in a progressively curved configuration in a plan view and a planar disposition in an elevational view. The slots are formed in the brackets, and the brackets are disposed on the patient's teeth, with the desired parameters by determining the mesiodistal profile (or thickness) of each tooth in the patient's mouth between the tip of the tooth and the gum.

SUMMARY OF THE INVENTION

This invention discloses and claims a method of determining parameters, such as depths and angles of slots in brackets and the positioning of the brackets on a patient's teeth, to obtain a disposition of an arch wire in the slots in the brackets in a progressively curved configuration in a plan view and a planar disposition in an elevational view. However, the method of this invention determines the parameters of the bracket slots and the bracket dispositions on the teeth to adjust the positioning of the teeth such that the buccal cusps in the mandibular molars and bicuspids become disposed in the marginal ridges in the maxillary molars and bicuspids when the patient closes his mouth to bite. The method of this invention accomplishes this by determining a number of specific parameters in each tooth, converting these determinations to data representative of such parameters and processing this data to determine the slot parameter and the bracket positioning for each tooth.

In one embodiment of the invention, a patient's teeth are adjusted in position to dispose the buccal cusps on the mandibular teeth against the marginal ridges on the maxillary teeth. To accomplish this, such contour parameters as the peaks of the buccal and lingual cusps, the depths of the grooves between such cusps and the intersection of the tooth with the gums may be determined for each of the patient's molars and bicuspids. Such determinations may then be converted to level orientations of the buccal and lingual cusp peaks for each molar and bicuspid. Such converted determinations may then be converted to data, preferably digital, representative of, and derived from, such determinations.

In each of the cuspids, laterals and centrals, such contour parameters as the lingual and facial incisal edge points and the intersection points with the gum may be determined and converted to orientation of the tooth perpendicular to the long axis of the tooth. Such determinations are then converted to data, preferably digital, representative of, and derived from, such determinations.

The data for each molar, bicuspid, cuspid, lateral and central is individually processed to determine bracket positions on such tooth and slot parameters, such as depth and angle, in such brackets to dispose an arch wire in the slots in the brackets of the different teeth in a continuously curved configuration in plan view and a planar disposition in elevational view. The slots are provided in the brackets, and the brackets are disposed on the patient's teeth, in accordance with such data processing.

DETAILED DESCRIPTION OF THE DRAWINGS

Figure 1:
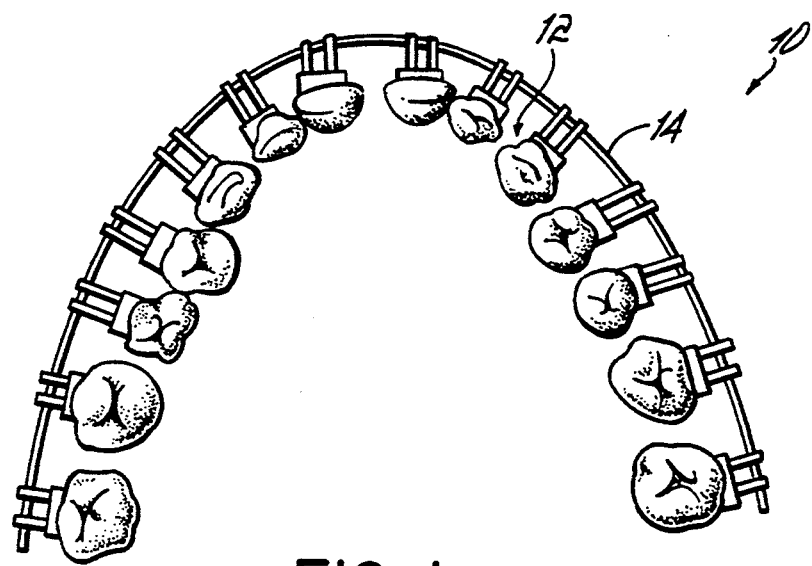
FIG. 1 is a schematic plan view illustrating the disposition of a brace on the teeth in a patient's mouth to adjust the disposition of the teeth in the patient's mouth.
Figure 2:
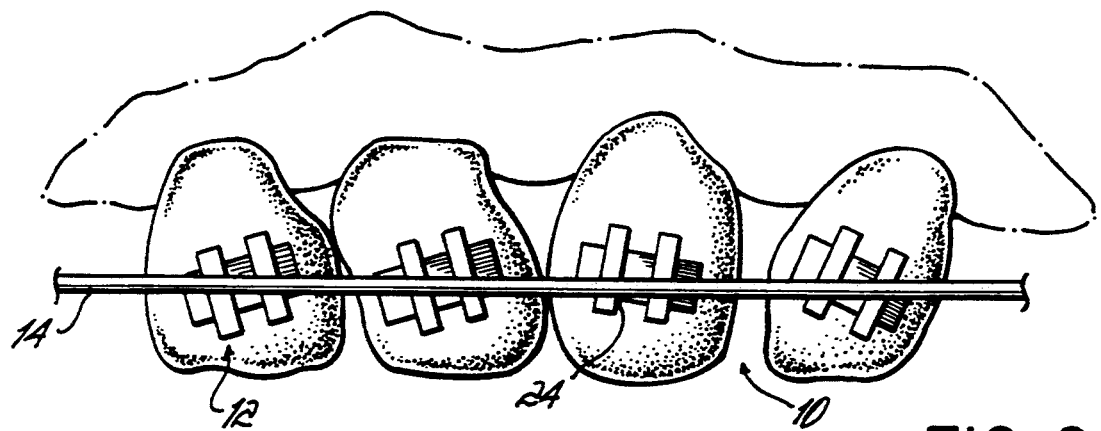
FIG. 2 is a fragmentary front elevational view schematically illustrating some of the teeth shown in FIG. 1 and the disposition of the brace on the teeth.

The method of this invention provides an optimal formation of a brace generally indicated at 10 in FIGS. 1 and 2. The brace 10 includes brackets generally indicated at 12 and an arch wire 14 supported by the brackets. The arch wire 14 is disposed in an arched configuration having a progressive curvature in a plan view (FIG. 1) and having a planar configuration in an elevational view (FIG. 2). In this way, there are no discontinuities in the arch wire 14 in either the plan or elevational view.

Figure 3:
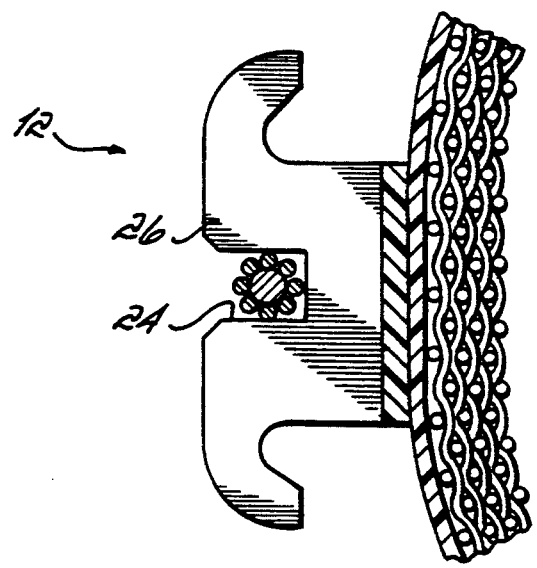
FIG. 3 is a schematic perspective view of a bracket included in the brace shown in FIG. 1 and illustrates the construction of the bracket and the disposition of a slot or groove in the bracket for receiving an arch wire included in the brace.

Each bracket 12 includes a pad 16 and a support member 18 (FIG. 3). The pads 16 and the support members 18 may be constructed in a manner disclosed and claimed in U.S. Pat. No. 4,068,399 issued to Frank R. Miller, Craig A. Andreiko and Kenneth R. Premo on Jan. 17, 1978, and U.S. Pat. No. 4,165,561 issued to Frank R. Miller, Craig A. Andreiko and Kenneth R. Premo on Aug. 28, 1979. The pads 16 and the support members 18 are made from a suitable material such as stainless steel. Stainless steel is desirable because it will not corrode in the patient's mouth. The pads 16 may preferably be in the form of a mesh.

Each of the pads 16 is bonded at one surface as by an adhering glue to the support member 18 and the other surface of the pad is bonded to one of the patient's teeth. Alternatively, the bracket may be constructed with an integral pad or bonding base. The support members 18 are provided with slots or grooves 24 in an outer surface 26 to receive the arch wire 14. The grooves 24 are provided with lengths, depths and widths, and may be angled, to receive the arch wire 14 such that the arch wire exerts forces on the patient's teeth to move the teeth to a configuration predetermined by the patient's orthodontist.

To perform the method constituting this invention, a patient's orthodontist provides a model, generally indicated at 30 (FIG. 1) of the teeth in the patient's mouth as such teeth actually appear, from the standpoint of positioning and configuration, in the patient's mouth. This may be provided by having the patient bite into a plasticizable material to define a female mold. This mold is then used to form the model 30. The orthodontist also provides a prescription of a desired positioning and configuration of the teeth in the patient's mouth. The dentist supplies the mold and the prescription to a laboratory, which then performs the steps in the method of this invention.

As a first step in the method of this invention, a laboratory determines certain parameters for each tooth in the patient's mouth from the model 30. FIG. 10 illustrates apparatus, generally indicated at 40, for determining the contour of each tooth in the model 30, these teeth being illustrated schematically in FIGS. 4–9. As shown in FIG. 10, the apparatus 40 includes a platform 44 for supporting the model 30 in a manner so that any selected tooth 42 in the model 30 can rest on the platform. A probe 46 is supported on a stanchion 48 for movement in the vertical direction. The probe 46 is accordingly movable downwardly in FIG. 10 to contact the tooth 42 whose contour is being determined. This is indicated by an arrow 50 in FIG. 10. The platform 44 is movable horizontally, as indicated by the arrows 54, simultaneously with the movement of the platform vertically to probe the contour of the tooth 42 and to determine the desired parameters of such tooth. The desired parameters for different teeth in the patient's mouth are shown schematically in FIGS. 4a–4b through FIGS. 9a–9b and will be described in detail subsequently.

Figure 4A:
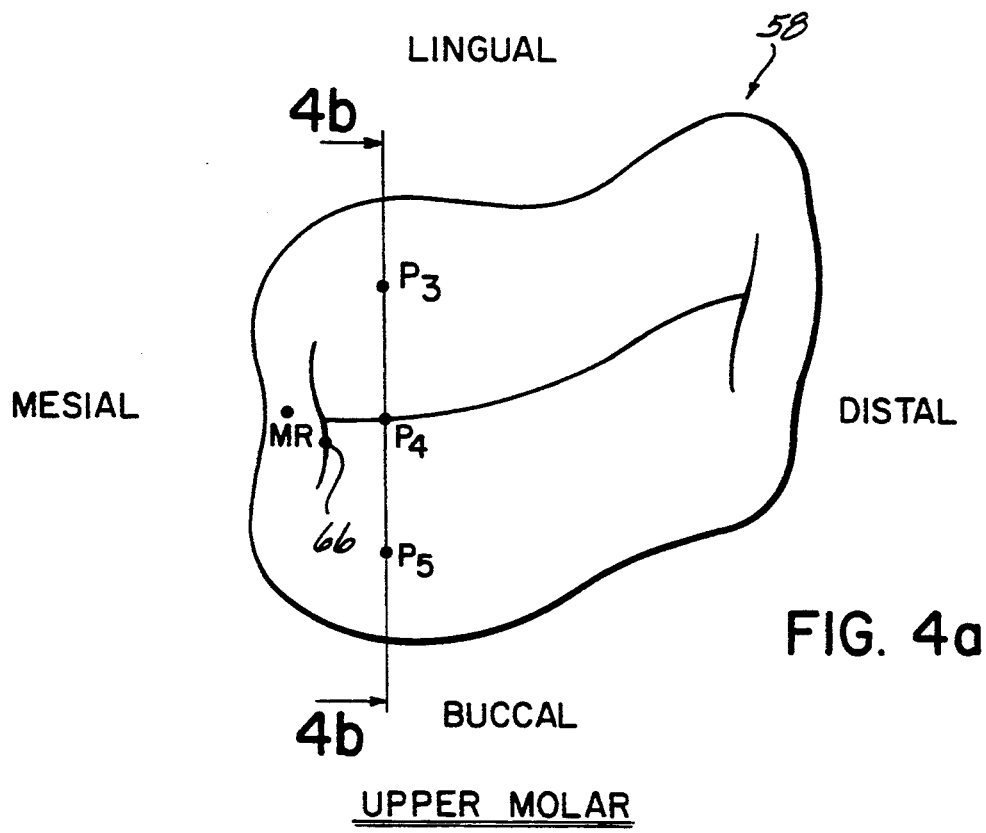
FIGS. 4a and 4b are respectively bottom plan and side elevational views of a typical upper molar in a patient's mouth and illustrates the method of determining the parameters used to determine the disposition of a bracket on such tooth and the parameters, such as depth and angle, of a slot or groove in such bracket.
Figure 4B:
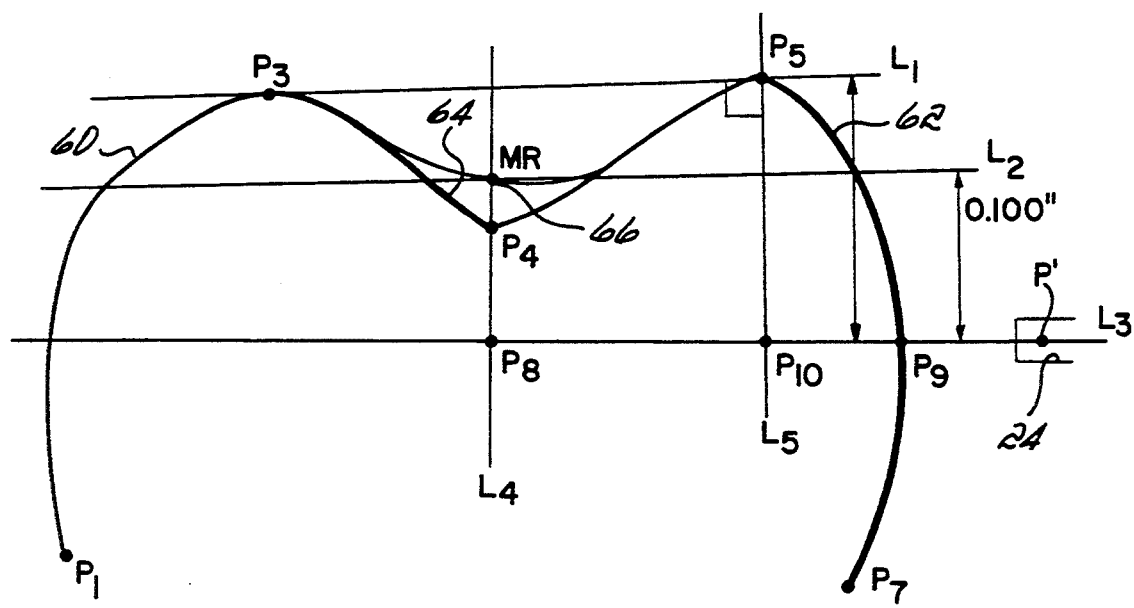

FIGS. 4a and 4b respectively constitute a bottom plan view and a side elevational view of a typical upper molar, generally indicated at 58, in a patient's mouth. As will be seen in FIGS. 4a and 4b, parameters are determined at strategic positions on the upper molar. These parameters may be converted to digital data and such data may be used to derive other parameters in digital form. The digital data measured and derived is processed to determine the disposition of a bracket 12 on the upper molar 58 and to determine such parameters as the depth and angle of a slot or groove 24 in the bracket.

As will be appreciated, the upper molar is provided with lingual cusps 60 and buccal cusps 62, with a central groove 64 between the lingual and buccal cusps and a marginal ridge 66 near the mesial end of the molar. As a first step in determining certain parameters and deriving other parameters in the upper molar 58, the upper molar is oriented schematically so that the tips of the mesial cusps (defined by the lingual and buccal cusps at the mesial end of the tooth) are level and in a line corresponding to a scan direction perpendicular to the long axis of the crown. The long axis of the tooth is defined as the line 60 extending between the mid point 63 between the cusps and the mid point 65 between the intersections of the molar with the patient's gum. The marginal ridge 66 is then plummeted and the anatomy or contour of the upper molar 58 at strategic positions in the upper molar is determined in a line corresponding to the most prominent part of the mesial cusp tips.

The determination of the contour or anatomy of the upper molar 58 includes the following:

P1—the point of lingual intersection of the molar 58 with the patient's gum
P3—the peak of the lingual cusp
P4—the depth of the central groove 64
P5—the peak of the buccal cusp
P7—the point of buccal intersection of the molar 58 with the patient's gum An analysis is made of various parameters in the molar 58 by using the pick points P1–P7 specified above. For example, the following parameters are determined digitally as by a microprocessor:

L1—a line through pick points P3 and P5
L2—a line extending through the marginal ridge point MR and parallel to the line L1
L3—a line parallel to the line L1 but typically displaced one tenth of an inch (0.100") from the line L2. This line defines a parameter P'. The distance of one tenth of an inch (0.100") has been used by applicant's assignee as a typical distance between the marginal ridge and the center of the arch wire when the arch wire is disposed in the groove 24 in the bracket 12 on the tooth.
L4—a line extending through the pick point P4 perpendicular to the line L2
P8—the point of intersection between the line L4 and the line L3
P9—the point of intersection between the line L3 and the external periphery of the molar 58
L5—a line through the pick point P5 and perpendicular to the line L1
P10—the point of intersection between the lines L3 and L5

From the above, the height of the bracket placement on the molar 58 can be determined as the distance between the points P5 and P10. The position of the bracket on the tooth can be determined as the position P9 since the points P9 and P10 are on the line L3. The position P' defining the center of the arch wire 14 in the slot 24 is determined as the distance between the points P8 and P9 plus 0.037". The distance of 0.037" has been typically used by applicants' assignee as the normal distance between the surface of the tooth and the center of the arch wire when the arch wire is disposed in the groove in the bracket on the tooth. This distance is determined by the thickness of the bracket at a position adjacent the slot 24 and by the radius (or half of the thickness) of the arch wire 14. The distance between MR (the marginal ridge) and the point P8 is the height of the marginal ridge relative to the slot 24 in the bracket 12 at a position half way between the top and bottom of the slot.

Figure 5A:
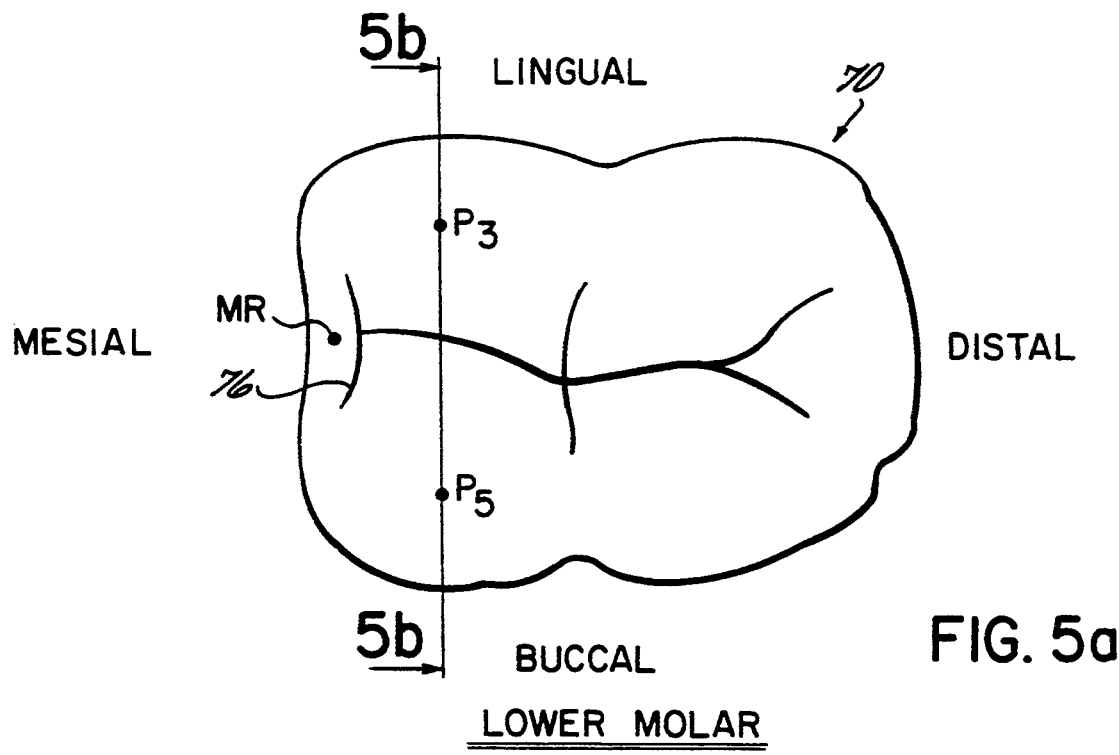
FIGS. 5a and 5b are respectively top plan and side elevational views of a typical lower molar in a patient's mouth and illustrates the method of determining the parameters used to determine the disposition of a bracket on such tooth and the parameters, such as depth and angle, of a slot in such brackets.
Figure 5B:
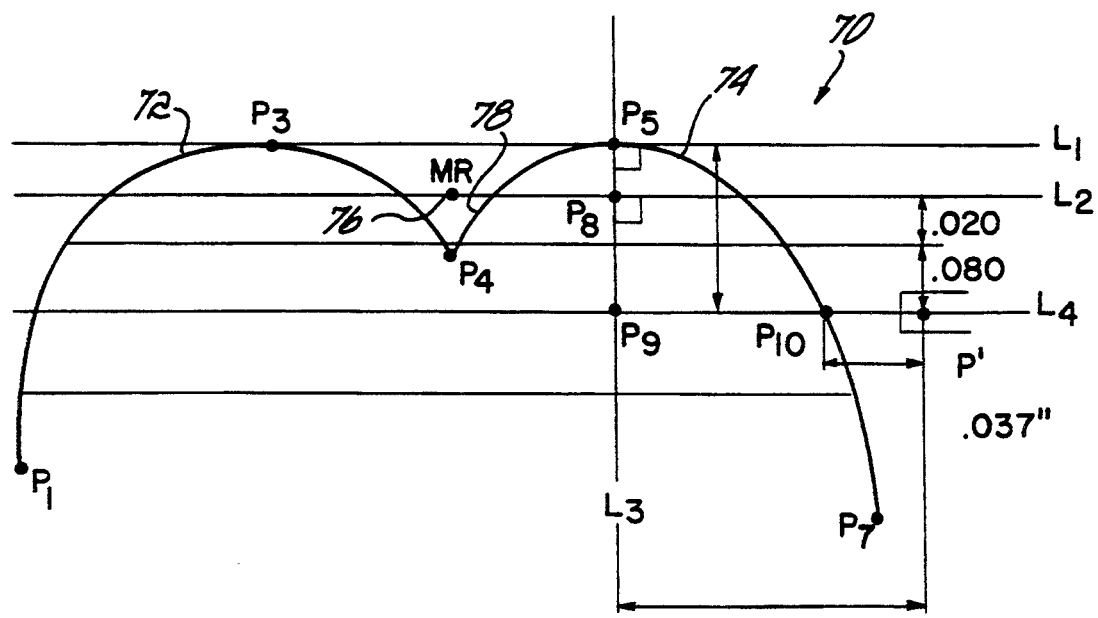

FIG. 5a constitutes an upper plan view of a typical lower molar generally indicated at 70 and FIG. 5b constitutes a side elevational view of such a typical lower molar. As with the upper molar 58, the lower molar 70 has lingual cusps 72 and buccal cusps 74, a marginal ridge 76 at the mesial end of the molar and a groove 78 between the cusps. The molar is initially oriented schematically so that the tips of the mesial cusps (defined by the cusps at the mesial end of the tooth) are level and in line in a scan direction perpendicular to the long axis of the molar. The marginal ridge MR is plummeted at the mesial end of the molar. In other words, the height reading of the marginal ridge MR at the mesial end of the molar 70 is determined. The anatomy or contour of the molar 70 is then determined in the lingual-buccal direction.

In determining the anatomy or contour of the lower molar 70, pick points are determined at strategic positions on the tooth. These include the following:

P1—the position of intersection of the lower molar 70 with the gum at the lingual end of the tooth P3—the peak of the lingual cusp 72
P4—the depth of the central groove 78 between the cusps 72 and 74
P5—the peak of the buccal cusp
P7—the point of intersection of the molar 70 with the patient's gum at the buccal end of the molar Other strategic positions are determined digitally as by a microprocessor from the pick points P1–P7. These include the following:

L1—a line drawn through the pick points P3 and P5
L2—a line through the marginal ridge MR parallel to the line L1
L3—a line through the pick point P5 perpendicular to the line L1
L4—a line parallel to L2 but displaced by the typical distance of one tenth of an inch (0.100") (the standard distance used by applicants' assignee) from the line L2 in the direction toward the gum
P8—the position defined by the intersection of lines L2 and L3
P9—the position of intersection of the lines L3 and L4
P10—the position on the line L4 where the buccal end of the molar 70 occurs
P'—a distance of 0.037" from the position P10. This is the position at which the median position of the arch wire 14 is located in the slot 24.

The parameters of the bracket positioning on the tooth and the slot in the bracket can be determined digitally as by a microprocessor from the parameters specified above. For example, the distance between the pick points P5 and P8 plus 0.100" defines the height of the middle point of the slot or groove 24 in the bracket when the bracket 12 is attached to the lower molar 70. The distance between the pick points P9 and P10 plus the typical distance of 0.037" (the standard distance used by applicants' assignee) defines the position P' for the lower molar 70. The position P' defines the center of the arch wire 14 in the slot 24.

Figure 6A:
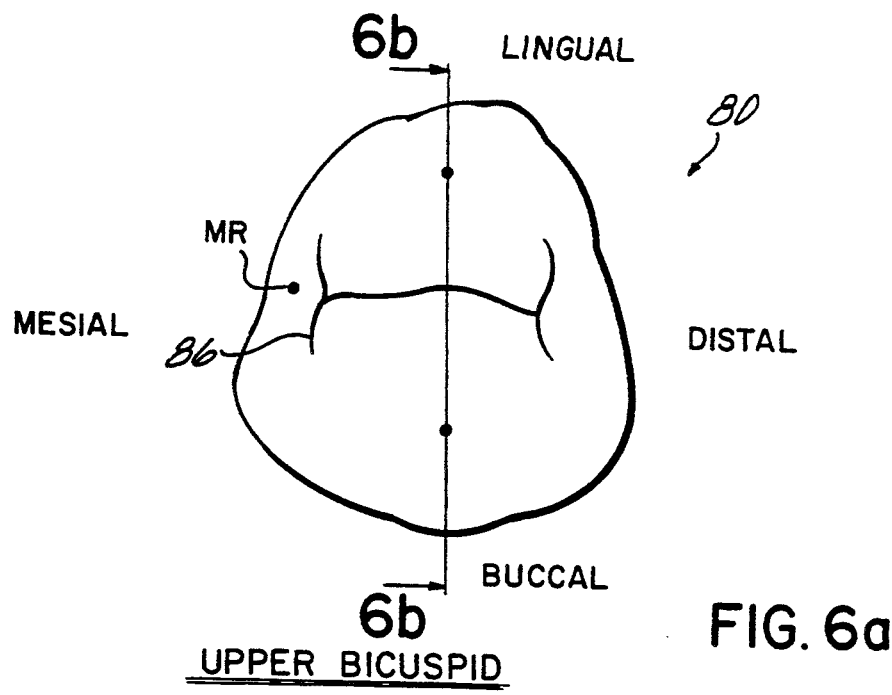
FIGS. 6a and 6b are respectively bottom plan and side elevational views of a typical upper bicuspid in a patient's mouth and illustrates the method of determining the parameters used to determine the disposition of a bracket on such tooth and the parameters, such as depth and angle, of a slot in such bracket.
Figure 6B:
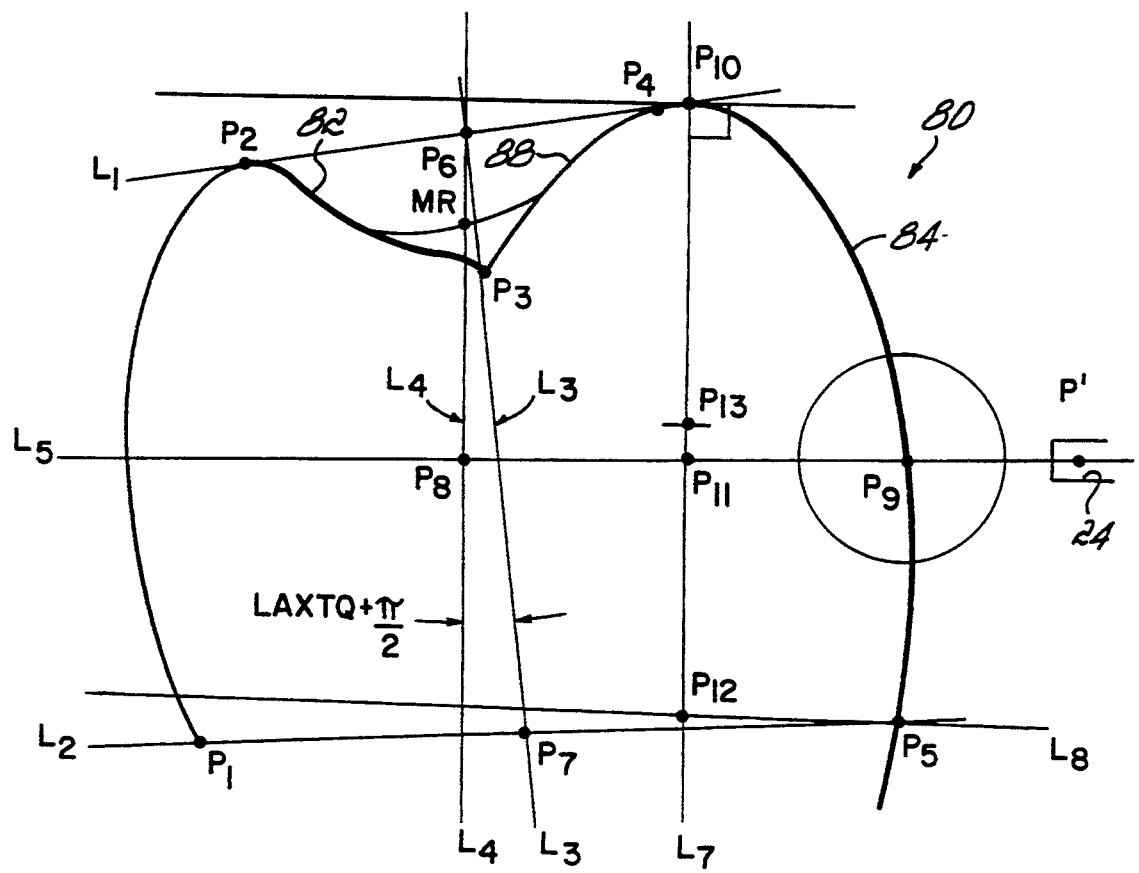

A typical upper bicuspid generally indicated at 80 is shown in bottom plan view in FIG. 6a and in side elevational view in FIG. 6b. The upper bicuspid includes lingual cusps 82 and buccal cusps 84, a marginal ridge 86 at the lingual end and a groove 88 between the buccal and lingual cusps. As with the upper molar shown in FIGS. 4a and 4b and the lower molar shown in FIGS. 5a and 5b, the upper bicuspid 80 is initially oriented schematically perpendicular to the long axis of the bicuspid. As with the upper molar 58, the long axis of the upper molar is determined by extending a line from the midpoint between the peaks of the tips of the lingual and buccal cusps and the midpoint between the points of lingual and buccal intersection with the gum. The marginal ridge 86 is then plummeted to determine the height of the marginal ridge at the mesial end of the bicuspid. The anatomy or contour of the tooth is then determined in a line corresponding to the most prominent part of the cusp tips in the bicuspid.

The determination of the contour of the bicuspid 80 includes a determination of the following pick points:

P1—the position at which the bicuspid 80 intersects the gum at the lingual end of the bicuspid
P2—the peak of the tip of lingual cusp 82
P3—the depth of the central groove 88 between the lingual and buccal cusps
P4—the peak of the tip of the buccal cusp 84
P5—the position at which the bicuspid intersects the gum at the buccal end of the bicuspid The pick points specified in the previous paragraph are processed, preferably digitally, as by a microprocessor to determine other parameters. This processing determines the following parameters derived from the pick points discussed above:

L1—a line through the pick points P2 and P4
L2—a line through the pick points P1 and P5
P6—the midpoint between the pick points P2 and P4 on the line L1
P7—the midpoint between the pick points P1 and P5 on the line L2
L3—a line through P6 and P7. This constitutes the long axis of the bicuspid 80
L4—a line extending through P6 and the marginal ridge MR as seen in FIG. 6b
P8—a position on the line L4 downwardly from the marginal ridge MR at the ridge slot height, which has been previously known
L5—a line perpendicular to line L4 through point P8
P9—the intersection of line L5 and the external periphery of the bicuspid 80
L6—a line parallel to L5 and extending through the most incisal point (or the peak of the upper projecting of the two cusps) of the bicuspid 80
P10—the position where the line L6 intersects the bicuspid 80
L7—a line extending through the point P10 perpendicular to the line L6
P11—the point of intersection of the lines L5 and L7
L8—a line extending through the point P5 perpendicular to the line L7
P12—the point of intersection between the lines L7 and L8
P13—the midpoint between the points P10 and P12 on the line L7
P'—a distance from the point P8 on the line L5 corresponding to the distance on the line L3 between the points P8 and P' for the upper molar shown in FIGS. 4 and 4b. This causes the marginal ridge point MR on the upper bicuspid to be aligned with the marginal ridge point MR on the upper molar.

The distance between the points P10 and P13 defines the position of the bracket 12 as determined by Andrews. As will be seen, the distance between the points P10 and P11 on the line L7 is the distance to the vertical center of the slot 24 in the bracket 12. This defines the vertical positioning of the bracket 12 on the bicuspid 80. The distance between the points P11 and P13 defines the difference in the positioning of the bracket 12 on the bicuspid 80 by applicant and the positioning of the bracket 12 on the bicuspid 80 by Andrews in the prior art. The distance between the marginal ridge 86 and the point P8 defines the position of the median position of the slot 24 between the upper and lower walls defining the slot. It also defines the median position of the wire 14 in the slot 24.

Figure 7A:
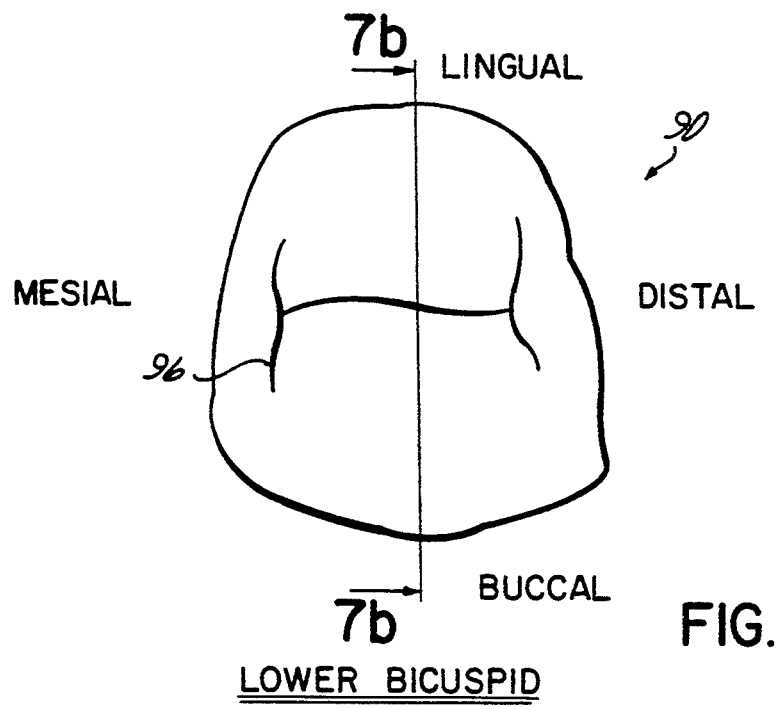
FIGS. 7a and 7b are respectively top plan and side elevational views of a typical lower bicuspid in a patient's mouth and illustrates the method of determining the parameters used to determine the disposition of a bracket on such tooth and the parameters, such as depth and angle, of a slot in such bracket.
Figure 7B:
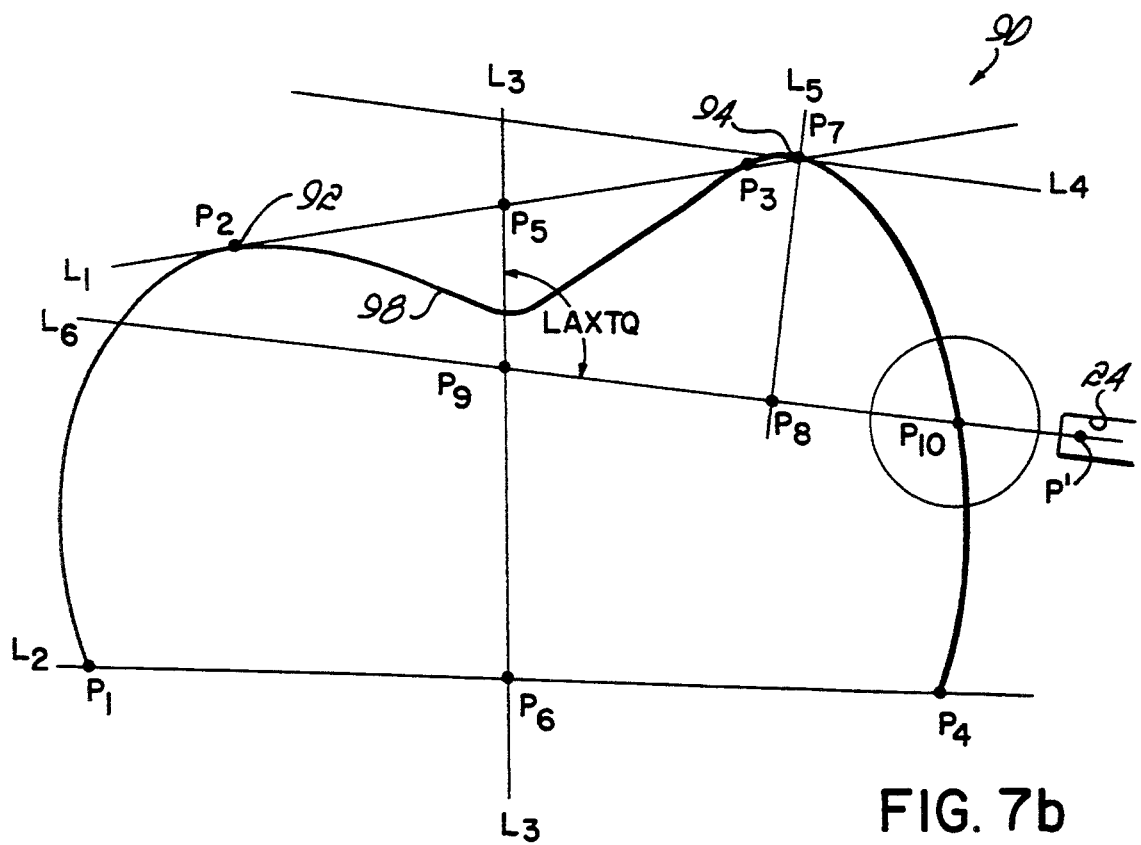

FIGS. 7a and 7b respectively show a top plan view and a side elevational view of a typical lower bicuspid generally indicated at 90. The lower bicuspid 90 is shown as including lingual cusps 92 and buccal cusps 94, a marginal ridge 96 at the lingual end and a groove 98 between the buccal and lingual cusps. The lower bicuspid 90 is initially oriented schematically perpendicular to the long axis of the bicuspid. The long axis is as described above with respect to the upper molars and the upper bicuspids. The anatomy or contour of the tooth is then determined in a line corresponding to the most prominent tip of the cusps on the lower bicuspid 90.

The following parameters are determined in the contour or anatomy of the lower bicuspid 90 in the line corresponding to the most prominent tip of the cusps on the lower bicuspid:

P1—the position at which the bicuspid 90 intersects the patient's gum at the lingual end of the bicuspid
P2—the peak position on the lingual cusp
P3—the peak position on the buccal cusp
P4—the position at which the bicuspid 90 intersects the patient's gum at the buccal end of the bicuspid Other parameters are determined by processing digitally, with the use of a microprocessor, the parameters specified above. These include the following:

L1—the line through the points P2 and P3
L2—the line through the points P1 and P4
P5—the mid point between the points P2 and P3 on the line L1
P6—the midpoint between the points P1 and P4 on the line L2
L3—the line through the points P5 and P6. This line may be considered to constitute the long axis of the bicuspid
L4—a line, at an angle LAXTQ relative to the line L3, through a position P7 constituting the tangential position on the bicuspid at the most incisal position on the bicuspid
P7—the peripheral position on the bicuspid 90 constituting the point of contact with the line L4 and also constituting the most incisal position on the bicuspid
L5—the line perpendicular to the line L4 through the position P7
P8—the position extending from the position P7 on the line L5, as known for the lower molar, to define the vertical position of the center of the slot 24 in the bracket 12
L6—the line perpendicular to the line L5 through the position P8
P9—the position of intersection between the lines L3 and L6
P10—the position at which the line L6 intersects the periphery of the bicuspid 90
P'—the position at which the median position on the arch wire 14 is disposed in the slot 24. This position is a distance along L6 from P8, the distance being defined by the distance along L6 from P9 to P' on the lower molar.

Figure 8A:
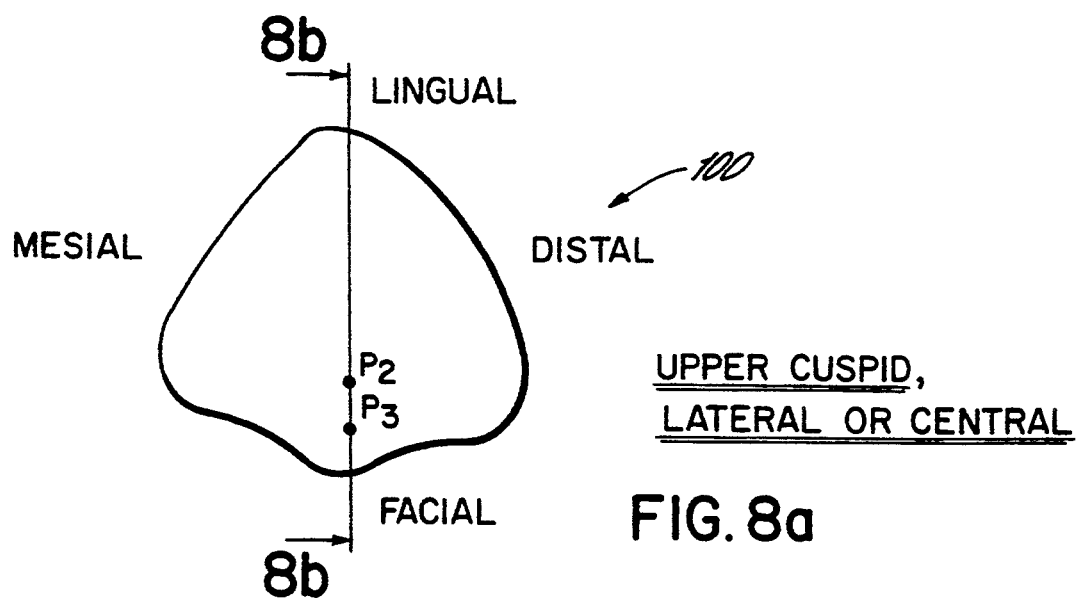
FIGS. 8a and 8b are respectively bottom plan and side elevational views of a typical upper cuspid, lateral or central in a patient's mouth and illustrates the method of determining the parameters used to determine the disposition of a bracket on such tooth and the parameters, such as depth and angle, of a slot in such bracket.
Figure 8B:
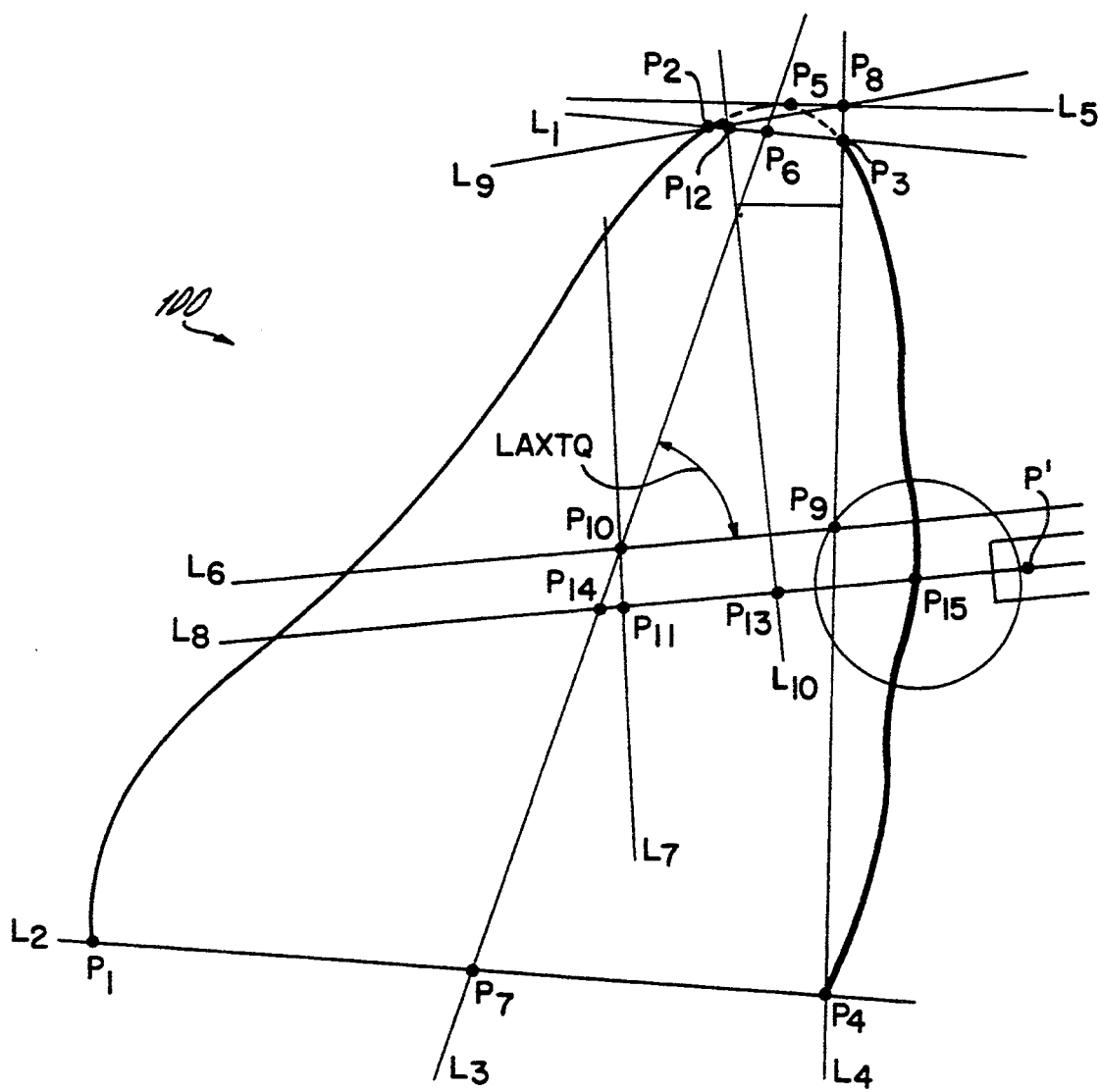

A typical upper cuspid, lateral or central generally indicated at 100 is illustrated in a bottom plan view in FIG. 8a and in a side elevational view in FIG. 8b. To determine the anatomy or contour of the upper cuspid, lateral and central 100, the tooth is oriented perpendicular to the long axis of the cuspid. The long axis of the tooth is defined as the line between the upper and lower extremities of the tooth or as the line between the upper tip of the tooth and the mid point between the positions of intersection of the tooth with the gum. The anatomy or contour of the tooth is then traced in a line at the most prominent point on the cuspid. In tracing this contour or anatomy, strategic pick points are determined. These include the following:

P1—the point of intersection of the cuspid, lateral or central 100 with the patient's gum at the lingual end of the cuspid, lateral or central
P2—the incisal edge of the cuspid, lateral or central 100 at the lingual end of the tooth
P3—the incisal edge of the cuspid, lateral or central 100 at the facial end of the tooth
P4—the point of intersection of the cuspid, lateral or central 100 with the patient's gum at the facial end of the tooth
P5—the theoretical position of the peak of the cuspid, lateral or central 100 before the wear or attrition of the tooth to the incisal edges P2 and P3. This position is determined by extending the contour of the cuspid, lateral or central 100 upwardly beyond the incisal edges P2 and P3.

The pick points specified above may be determined on a digital basis and are then digitally processed as in a microprocessor to determine a number of additional parameters. These include the following:

L1—the line through the points P2 and P3
L2—the line through the points P1 and P4
P6—the midpoint between the points P2 and P3 on the line L1
P7—the midpoint between the points P1 and P4 on the line L2
L3—the line through the points P6 and P7, this line constituting the long axis of the tooth
L4—the line through the points P3 and P4
L5—the line through the point P5 and perpendicular to the line L4
P8—the point common to the lines L4 and L5
P9—the midpoint on the line L4 between the points P4 and P8
L6—a line obtained by rotating the line L3 about the point P10 as a fulcrum until the rotated line passes through the point P9, the angle between the lines L3 and L4 being designated as LATQX. The angle LATQX is the angle between the long axis and the line defining the disposition of the arch wire on the tooth
P10—the point of intersection between the lines L3 and L6
L7—the line through the point P10 perpendicular to the line L6
P11—the bracket placement height discrepancy relative to the point P10 on the line L7. The distance between the points P10 and P11 on the line L7 is the distance between the bracket placement by Andrews and the bracket placement by applicant. This distance may be one tenth of an inch (0.100").
L8—the line through the point P11 perpendicular to the line L7
L9—the line parallel to the line L8 and passing through the incisal edge P2
P12—the point of intersection of the line L9 and the incisal tooth surface of the cuspid cuspid, lateral or central 100
L10—the line through the point P12 perpendicular to the line L9
P13—the point of intersection between the lines L8 and L10
P14—the point of intersection between the lines L3 and L8
P15—the point of intersection between the line L8 and the tooth surface The distance between the points P12 and P13 is the bracket placement height vertically in applicant's invention. The distance between the points P8 and P9 is the bracket placement height vertically in the prior art as represented by Andrews.

The position P' is the center of the arch wire 14 in the slot 24. It is the distance from the point P13 on the line L8 corresponding to the distance on the line L5 from the point P11 to the point P' for the upper bicuspid shown in FIGS. 6a and 6b. In this way, the tip of the upper cuspid, lateral and central can be aligned with the cusp of the upper bicuspid.

Figure 9A:
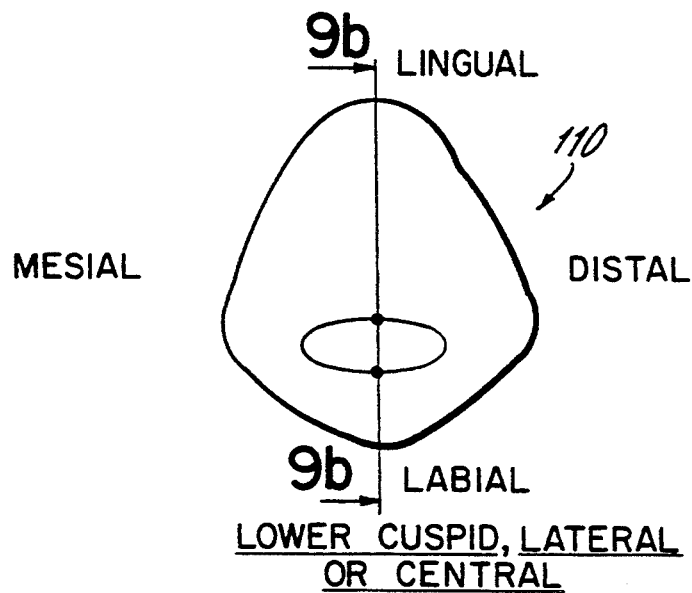
FIGS. 9a and 9b are respectively top plan and side elevational views of a typical lower cuspid, lateral or central in a patient's mouth and illustrates the method of determining the parameters used to determine the disposition of a bracket on such tooth and the parameters, such as depth and angle, of a slot in such bracket.
Figure 9B:
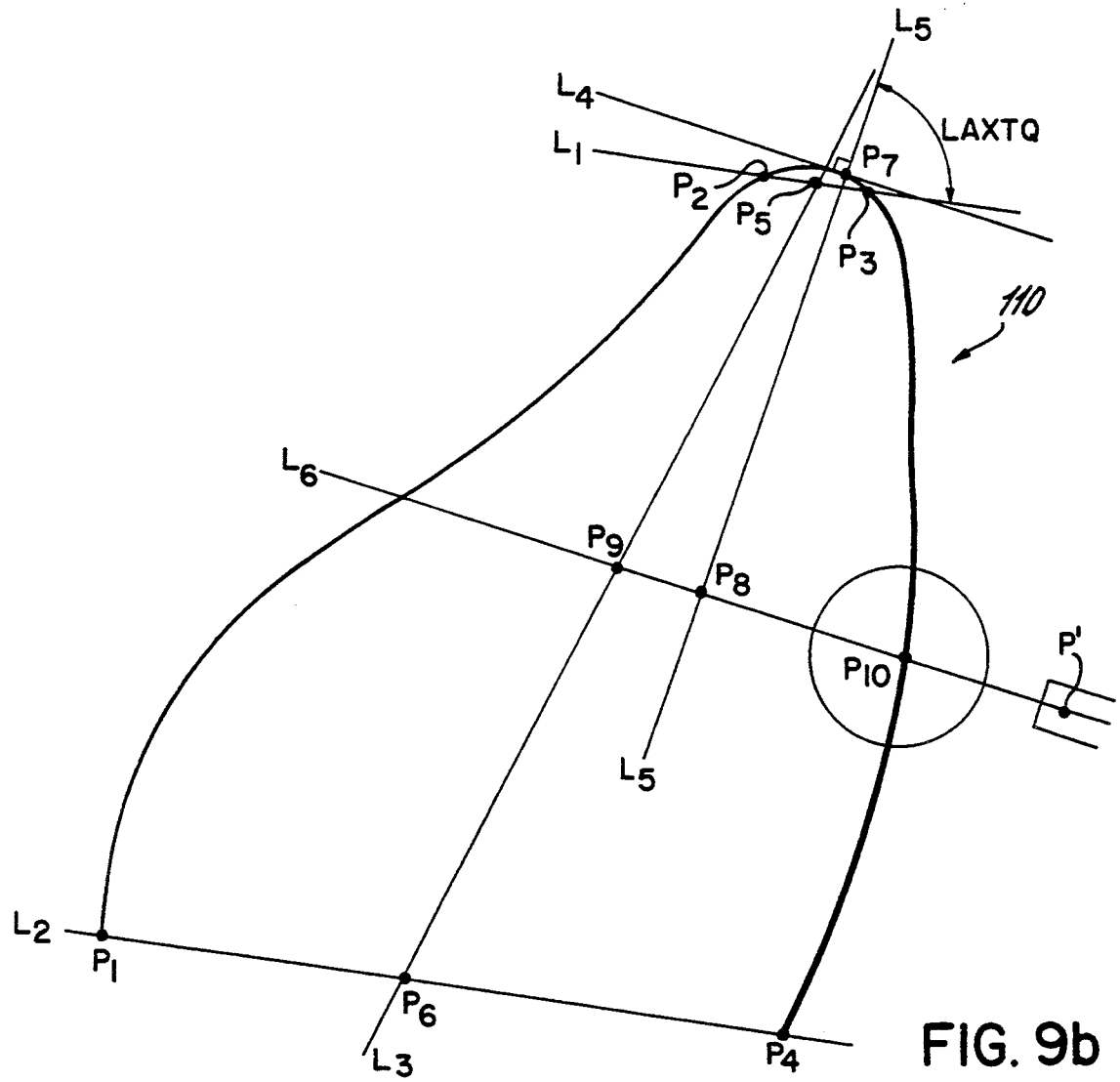
Figure 10:
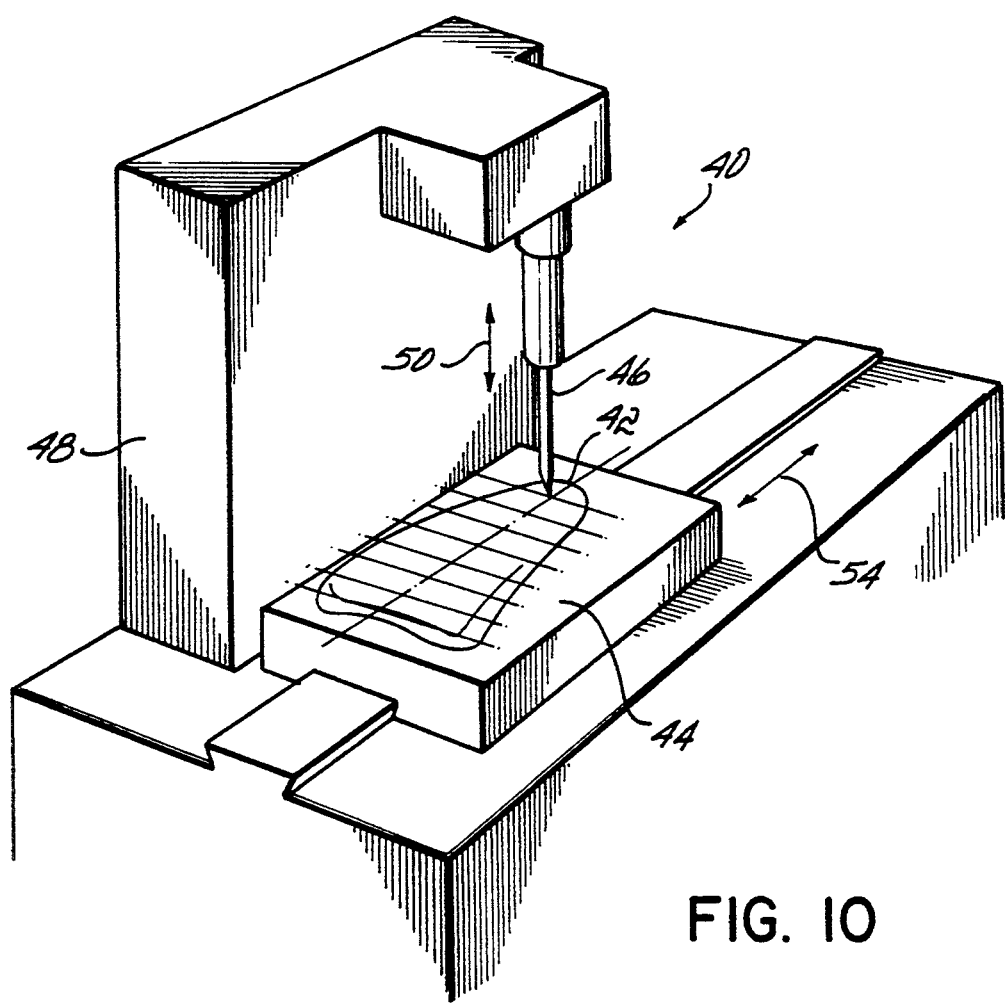
FIG. 10 is a schematic perspective view of equipment which may be used to determine the contour of the teeth, such as those shown in FIGS. 4–9, in a patient's mouth.
Figure 11:
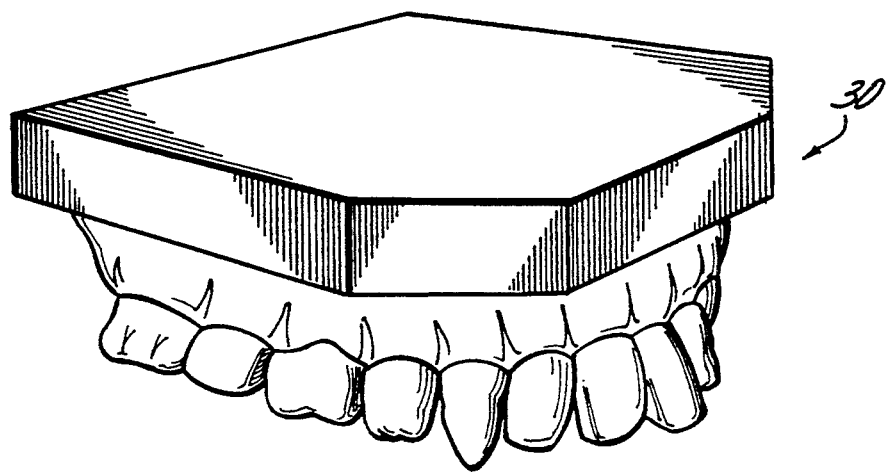
FIG. 11 is a perspective view of a mold of the teeth in a patient's mouth, this mold being used to provide the parameters for the brackets attached to the teeth in FIGS. 4–9.

A typical lower cuspid, lateral or central generally indicated at 110 is shown in top plan view in FIG. 9a and in side elevational view in FIG. 9b. The lower cuspid, lateral or central 110 is initially oriented perpendicular to the long axis and the anatomy or contour is traced at the positions of prominence on the cuspid, lateral or central. During such tracing, the pick points at strategic positions on the cuspid, lateral or central 110 are determined preferably digitally. These include the following:

P1—the position of intersection of the cuspid, lateral or central 110 with the patient's gum at the lingual end of the cuspid, lateral or central P2—the point of the lingual incisal edge P3—the point of the facial incisal edge P4—the point of intersection of the cuspid, lateral or central 110 with the patient's gum at the facial end of the cuspid, lateral or central The pick points specified above are then processed, preferably digitally, as by a microcomputer to determine a number of additional parameters in the cuspid, lateral or central 110. These include the following:

L1—the line through the pick points P2 and P3

L2—the line through the pick points P1 and P4

P5—midpoint between the pick points P2 and P3 on line L1

P6—the midpoint between the pick points P1 and P4 on the line L2

L3—the line through the pick points P5 and P6, this line constituting the long axis of the cuspid, lateral or central 110

L4—the line extending through the most incisal tooth contact (the top peripheral position on the cuspid, lateral or central 110) at an angle LAXTQ to the line L3

P7—the point at which the line L4 intercepts the most incisal position on the cuspid, lateral or central 110

L5—the line through the point P7 perpendicular to the line L4

P8—the point downwardly on the line L5 from the point P7 by a distance corresponding to the median position vertically in the slot 24

L6—the line through the point P8 on the lower first molar perpendicular to the line L5

P9—the point of intersection between the lines L3 and L6

P10—the point of intersection of the line L6 with the facial periphery of the cuspid, lateral or central 110

P'—the distance on the line L6 between the points P8 and P10+0.037", this constituting the center of the arch wire 14 in the groove 12 in the bracket. This position is a distance along L6 from P8, this distance being defined as the distance along L4 from P9 to P' on the lower molar.

Typical values for the angle LAXTQ for different teeth are as follows:

| | Maxillary (Degrees) | Mandibular (Degrees) |
|---|---|---|
| Central | 63 | 73 |
| Lateral | 68 | 73 |
| Cuspid | 72 | 80 |
| First Biscuspid | 86 | 97 |
| Second Biscuspid | 86 | 100 |

Exhibit A is attached to this application and is considered as forming a part of this application. Exhibit A sets forth a program which may be used to implement the method described above.

A method is accordingly disclosed for determining the position of the brackets 12 on typical molars, bicuspids, cuspids, laterals and centrals in a patient's mouth and of determining the parameters of the slots 24 in the brackets 12 including the positions of the slots 24 in the brackets 12 for such typical molars, bicuspids, cuspids, laterals and centrals. The positions of the brackets 12 on the teeth and of the slots in the brackets are located so that the arch wire 14 disposed in the slots 24 in the brackets 12 has a planar disposition in an elevational view and a progressive curvature in a plan view.

The positions of the brackets on the teeth compensate for the fact that each tooth may have an individual height relative to adjacent teeth. Such parameters as the depths of the slots 24 in the brackets 12 compensate for different thicknesses of adjacent teeth and for the recesses of individual teeth relative to adjacent teeth in the patient's mouth. The slots in adjacent brackets are angled relative to one another to insure that the arch wire will have a planar configuration in elevation and a progressive curvature in plan when the arch wire is disposed in the slots in the brackets on the teeth in the patient's mouth.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

We claim:

1. A method of forming an orthodontic brace for positioning teeth of a patient, the method comprising the steps of:

digitally representing individual teeth of the patient each by a contour in a vertical labial-facial plane;

simplifying the contours by selecting parameters of prominences of each of the respective teeth, including parameters representing each selected prominence by coordinate data, including vertical and horizontal-lingual-facial components of the prominences on the contour, of:

a lingual tooth gum intersection point and a facial tooth gum intersection point, for posterior ones of the teeth, a mesial-buccal cusp tip, a mesial lingual cusp tip, and, additionally for at least the upper posterior teeth, a mesial marginal ridge point, and, for anterior ones of the teeth, a lingual incisal edge point and a facial incisal edge point;

selecting an arcuate shape for an orthodontic brace;

digitally calculating with a processor positions of contours and of the coordinate data for the parameters of individual teeth relative to the arcuate shape of the brace to place the parameters of the teeth in desired positions relative to the parameters of others of the teeth;

digitally calculating with a processor locations on the contours of the individual teeth for connection of the orthodontic brace thereto;

digitally calculating with a processor geometry, including dimensional parameters, of the orthodontic brace for connection at the locations on the teeth such that, when the brace is attached to the respective tooth at the calculated location thereon, the brace will exert forces on the teeth to move the teeth to the desired relative positions; and fabricating the brace in accordance with the calculated geometry.

2. A method of forming an orthodontic brace for positioning teeth of a patient, the method comprising the steps of:

digitally representing individual teeth of the patient by digital data defining a contour in a vertical labial-facial plane;

digitally deriving for each of the teeth, from the digital data, additional parameters including a crown long axis of the tooth;

digitally representing orientations of the derived crown long axes of the teeth in their respective lingual-facial planes to desired torque angles;

digitally calculating, with a processor, geometry, including dimensional parameters of an orthodontic brace for connection at locations on each of the teeth relative to the contours thereof such that, when the brace is attached to the respective teeth at the locations, the brace will exert forces on the teeth to move the crown long axes of the teeth to the desired torque angles; and fabricating an orthodontic brace in accordance with the calculated geometry.

3. The method of claim 2 wherein:

the contour defining data includes vertical horizontal-lingual-facial coordinate data including:

a lingual tooth gum intersection point, a facial tooth gum intersection point, for posterior ones of the teeth, a mesial-buccal cusp tip and a mesial lingual cusp tip, and for anterior ones of the teeth, a lingual incisal edge point and a facial incisal edge point;

the crown long axes deriving step includes:

for posterior teeth, constructing a line through a midpoint between the tooth gum intersection parameters and through a midpoint of between the cusp tip parameters on the contour, and for anterior teeth, constructing a line through a midpoint between the tooth gum intersection parameters and a midpoint between the incisal edge point parameters on the contour.

4. The method of claim 3 wherein:

the crown long axis orienting step includes the step of mathematically orienting the axis of each tooth in accordance with a predefined set of values for the teeth.

5. The method of claim 4 wherein:

the axis orienting step includes the step of orienting each crown long axis to a predefined set of angles relative to the horizontal approximately equal to:

for lower centrals, 63°,
for lower laterals, 68°,
for lower cuspids, 72°,
for lower first bicuspids, 86°,
for lower second bicuspids, 86°,
for upper centrals, 73°,
for upper laterals, 73°,
for upper cuspids, 80°,
for first bicuspids, 97°, and
for second bicuspids, 100 °.

6. The method of claim 5 wherein:

the axis orienting step includes the step of orienting the crown long axes for molars to angles, relative to the horizontal, that set the mesial cusp tips thereof level.

7. A method of forming an orthodontic brace for positioning teeth of a patient, the method comprising the steps of:

digitally representing individual teeth of the patient by digital data defining a contour in a vertical labial-facial plane;

simplifying the contour by defining coordinate data locating points thereon including:

for each tooth, a lingual tooth gum intersection point and a facial tooth gum intersection point, for posterior ones of the teeth, also a mesial-buccal cusp tip and a mesial lingual cusp tip, and for anterior ones of the teeth, also a lingual incisal edge point and a facial incisal edge point;

digitally deriving, with a processor from the digital data, a crown long axis of individual teeth:

for posterior teeth, through a midpoint between the tooth gum intersection parameters and through a midpoint of between the cusp tip parameters on the contour, and for anterior teeth, through a midpoint between the tooth gum intersection parameters and a midpoint between the incisal edge point parameters on the contour;

digitally calculating, with a processor, geometry, including dimensional parameters, of the orthodontic brace for connection at locations on the contours of the individual teeth such that, when the brace is attached to the respective teeth, the brace will exert forces on the teeth to relatively position the teeth with respect to the derived crown long axes of the teeth; and fabricating the brace in accordance with the calculated geometry.

8. A method of forming an orthodontic brace for positioning teeth of a patient, the method comprising the steps of:

digitally representing individual teeth of the patient each by a counter that includes coordinates of parameters corresponding to prominences of the tooth;

digitally defining a generally horizontal archwire plane;

digitally representing the vertical position of the archwire plane relative to of at least one of the prominences of a selected one of the teeth such that the plane intersects the contour;

digitally deriving vertical positions, relative to at least one of the prominences of the respective teeth, of the intersections of the archwire plane with the contours of a plurality of the teeth other than the selected one of the teeth that will vertically locate the prominences of the respective teeth relative to the prominences of the selected one of the teeth;

digitally calculating with a processor, for the selected one of the teeth and each of the teeth of the plurality, the geometry of a bracket to be mounted at an attachment position at the intersection of the archwire plane and the contour of the tooth, for connecting the tooth to an archwire disposed in the archwire plane so that, when the brackets are attached at the attachment positions on the respective teeth and connected to the archwire, forces will be exerted on the teeth to move the teeth to desired relative positions; and fabricating brackets in accordance with the calculated bracket geometries.

9. The method of claim 8 further comprising the step of:

establishing the bracket attachment positions at the intersections of the contours of the teeth with the archwire plane.

10. The method of claim 9 further comprising the step of:

selecting an archwire having an arcuate shape;

the bracket geometry calculating step including the step of calculating the dimensions of a slot in the brackets such that, when the brackets are mounted on the teeth at the attachment positions, the slot will lie in the archwire plane and have a depth extending to an archwire positioned in the archwire plane.

11. The method of claim 8 wherein:

the selected tooth is a molar;

the parameter coordinate defining step for the molar includes the step of defining the coordinates of the location of the mesial marginal ridge of the molar with respect to the contour of the molar; and the archwire plane locating step, for the molar, includes the step of mathematically locating the vertical position of the archwire plane relative to the contour of the molar at a predetermined height with respect to the mesial marginal ridge point thereof.

12. The method of claim 11 wherein:

the molar is an upper molar;

the plurality of other teeth include at least one upper bicuspid;

the parameter coordinate defining step for the bicuspid includes the step of defining the coordinates of the location of the mesial marginal ridge of the bicuspid with respect to the contour thereof; and the archwire plane locating step, for the bicuspid, includes the step of mathematically locating the vertical position of the archwire plane relative to the contour of the bicuspid at a height with respect to the mesial marginal ridge point of the bicuspid that is related to that of the molar.

13. The method of claim 8 wherein:

the selected tooth is a lower molar;

the parameter coordinate defining step for the molar includes the step of defining the coordinates of the location of the mesial buccal cusp tip of the molar with respect to the contour of the molar; and the method further comprises the step of calculating a vertical distance from the archwire plane to the mesial buccal cusp tip of the molar.

14. The method of claim 13 wherein:

the plurality of other teeth include at least one lower bicuspid;

the parameter coordinate defining step for the bicuspid includes the step of defining the coordinates of the location of a mesial buccal cusp tip with respect to the contour thereof; and the archwire plane locating step for the bicuspid includes the step of mathematically locating the vertical position of the archwire plane a vertical distance relative to the buccal cusp tip of the bicuspid that is related to that of the molar.

15. The method of claim 13 wherein:

the plurality of other teeth include at least one lower anterior tooth;

the parameter coordinate defining step for the anterior tooth includes the step of defining the coordinates of the location of an incisal peak with respect to the contour thereof; and the archwire plane locating step for the anterior tooth includes the step of mathematically locating the vertical position of the archwire plane a vertical distance relative to the incisal peak of the anterior tooth that is related to the distance of the mesial buccal cusp tip of the molar relative to the archwire plane.

16. The method of claim 15 further comprising the step of:

digitally deriving for the anterior tooth an extension of the contour containing a pre-attrition peak of the tooth prior to wear thereof;

the parameter coordinate defining step for the anterior tooth includes the step of defining the coordinates of the location of the incisal peak as the pre-attrition peak.

17. A method of forming an orthodontic brace for positioning teeth of a patient, the method comprising the steps of:

digitally representing individual teeth of the patient by a contour that includes coordinates of parameters corresponding to prominences of the tooth, including the coordinates corresponding to a mesial marginal ridge point on a selected posterior tooth;

digitally defining the vertical position of a bracket attachment location relative to the contour of the selected posterior tooth at a predetermined vertical distance from the marginal ridge point thereof;

digitally deriving, with a processor, vertical positions of bracket attachment locations relative to the contours of a plurality of the teeth other than the selected posterior tooth at vertical distances relative to parameters thereof that have a specifically defined relationship to the predetermined vertical distance for the selected posterior tooth;

digitally calculating, for the selected tooth and each of tooth of the plurality, the geometry of a bracket to be mounted at the attachment position on each respective tooth, for connecting the teeth to an archwire so that, when the brackets are attached to the attachment positions on the respective teeth and connected to the archwire, forces will be exerted on the teeth to move the teeth to desired relative positions; and fabricating brackets in accordance with the calculated bracket geometry.

18. The method of claim 17 further comprising the steps of:

defining a generally horizontal archwire plane;

establishing the positions of the bracket attachment locations at the intersections of the contours of the teeth with the archwire plane.

19. The method of claim 18 further comprising the step of:

selecting an archwire having an arcuate shape;

the bracket geometry calculating step including the step of calculating the dimensions of a slot in each of the brackets such that, when the brackets are mounted on the teeth at the respective attachment locations, the slots will lie in the archwire plane and have depths extending to an archwire positioned in the archwire plane.

20. The method of claim 17 wherein:

the selected tooth is a molar;

the parameter coordinate defining step for the molar includes the step of defining the coordinates of the location of the mesial marginal ridge with respect to the contour thereof; and the bracket attachment location deriving step for the molar includes the step of mathematically locating the vertical position of the bracket attachment location thereof relative to the contour of the molar at a predetermined height with respect to the mesial marginal ridge point thereof.

21. The method of claim 20 wherein:

the molar is an upper molar;

the plurality of other teeth include at least one upper bicuspid;

the parameter coordinate defining step for the bicuspid includes the step of defining the coordinates of the location of the mesial marginal ridge with respect to the contour thereof; and the bracket attachment location deriving step for the bicuspid includes the step of mathematically locating the vertical position of the bracket attachment location relative to the contour of the bicuspid at a height with respect to the mesial marginal ridge point of the bicuspid that is related to that of the molar.

22. The method of claim 17 wherein:

the selected tooth is a lower molar;

the parameter coordinate defining step for the lower molar includes the step of defining the coordinates of the location of the mesial buccal cusp tip with respect to the contour thereof; and the method further comprises the step of calculating a vertical distance from the mesial buccal cusp tip of the lower molar to the bracket attachment location thereof.

23. The method of claim 22 wherein:

the plurality of other teeth include at least one lower bicuspid;

the parameter coordinate defining step for the lower bicuspid includes the step of defining the coordinates of the location of a mesial buccal cusp tip with respect to the contour thereof; and the bracket attachment location defining step for the bicuspid includes the step of mathematically locating the vertical position of the bracket attachment location at a vertical distance relative to the buccal cusp tip thereof that is related to that of the molar.

24. The method of claim 22 wherein:

the plurality of other teeth includes at least one lower anterior tooth;

the parameter coordinate defining step for the anterior tooth includes the step of defining the coordinates of the location of an incisal peak with respect to the contour thereof; and the bracket attachment location defining step for the anterior tooth includes the step of mathematically locating the vertical position of the bracket attachment location thereof at a vertical distance relative to the incisal peak thereof that is related to the distance of the mesial buccal cusp tip of the molar relative to the bracket attachment location thereof.

25. The method of claim 24 further comprising the step of:

digitally deriving for the anterior tooth an extension of the contour containing a pre-attrition peak parameter of the tooth representing an incisal peak thereof prior to wear;

the parameter coordinate defining step for the anterior tooth including the step of defining the coordinates of the location of the incisal peak as the pre-attrition peak.

26. A method of forming an orthodontic brace for positioning teeth of a patient, the method comprising the steps of:

digitally representing individual teeth of the patient each by a contour that includes a representation of prominences of the tooth, the contour for anterior ones of the teeth including a representation of an incisal peak on the anterior tooth;

digitally modifying, for at least one of the anterior teeth, the contour thereof to include a pre-attrition peak of the tooth as the incisal peak thereof;

digitally calculating with a processor, for each of the individual teeth, the geometry of a bracket to be mounted at an attachment position relative to the contour thereof, for connecting the teeth to an archwire so that, when brackets are attached to the attachment positions on a plurality of the teeth and connected to the archwire, forces will be exerted on the teeth to move the teeth to desired relative positions relative to the pre-attrition peak of the at least one anterior tooth; and fabricating brackets in accordance with the calculated bracket geometries.

27. The method of claim 26 further comprising the steps of:

establishing the position of the bracket attachment location on the anterior tooth relative to the pre-attrition peak thereof.

28. The method of claim 27 further comprising the step of:

selecting an archwire having an arcuate shape and establishing an archwire plane in which the archwire is to be positioned relative to the contours of the teeth;

the bracket geometry calculating step including the step of calculating the dimensions of a slot in each of the brackets such that, when the brackets are mounted on the teeth at the attachment locations, the slots have depths extending to an archwire positioned in the archwire plane.

29. A method of forming an orthodontic brace for positioning teeth of a patient, the method comprising the steps of:

digitally representing each of a plurality of individual teeth of the patient by a contour that includes prominences of the tooth, the contours for upper molars and bicuspids including a horizontal facial-lingual coordinate corresponding to a mesial marginal ridge point thereon and the contours for lower molars and bicuspids each including a horizontal facial-lingual coordinate of a mesial buccal cusp tip thereon;

defining bracket attachment locations relative to the contours of a plurality of the teeth including molars and bicuspids;

selecting an archwire having an arcuate shape;

determining the positions of upper and lower archwires in respective generally horizontal archwire planes;

digitally calculating with a processor, for upper molars and bicuspids, the geometries of brackets to be mounted at the attachment locations relative to the contours of the respective teeth, for connecting the teeth to the upper archwire so that, when the brackets are attached at the attachment locations to the respective teeth and connected to the upper archwire at its position in the upper archwire plane, forces will be exerted on the teeth to move the upper molars and bicuspids to desired relative positions at which their mesial marginal ridge points are at related horizontal distances from the upper archwire;

digitally calculating with a processor, for lower molars and bicuspids, the geometry of a bracket to be mounted at the attachment locations on the contours of the respective teeth, for connecting the teeth to the lower archwire so that, when the brackets are attached to the attachment locations on the respective teeth and connected to the lower archwire at its position in the lower archwire plane, forces will be exerted on the teeth to move the lower molars and bicuspids to desired relative positions at which their mesial buccal cusp tips are at related horizontal distances from the lower archwire and at the horizontal positions of the mesial marginal ridge points of the corresponding upper molars or bicuspids; and fabricating brackets in accordance with the calculated bracket geometry.

30. A method of forming an orthodontic brace for positioning teeth of a patient, the method comprising the steps of:

digitally representing each of a plurality of individual teeth of the patient by a contour that includes prominences of the respective tooth, the contours for upper first bicuspids including a horizontal facial-lingual coordinate corresponding to a mesial buccal cusp tip thereof, and the contours for upper anterior teeth including a horizontal facial-lingual coordinate corresponding to an incisal peak thereof;

defining bracket attachment locations relative to the contours of a plurality of the teeth including upper anterior teeth and first bicuspids;

defining a generally horizontal upper archwire plane;

selecting an upper archwire having an arcuate shape;

determining the position of an upper archwire in the upper archwire plane;

digitally calculating with a processor, for individual upper first bicuspids and anterior teeth, the geometries of brackets to be mounted at the attachment locations relative to the contours of the respective teeth, for connecting the teeth to the upper archwire so that, when the brackets are attached at the attachment locations to the respective teeth and connected to the upper archwire at its position in the upper archwire plane, forces will be exerted on the teeth to move the upper anterior teeth and first bicuspids to desired relative positions at which the incisal peaks of the upper anterior teeth are at horizontal distances from the upper archwire that are related to the horizontal distances of the mesial buccal cusp tips of the first bicuspids from the upper archwire; and fabricating brackets in accordance with the calculated bracket geometry.

31. The method of claim 30 further comprising the step of:

digitally modifying for at least one of the upper anterior teeth the contour thereof to include a pre-attrition peak of the tooth as the incisal peak thereof;

the forces exerted on the teeth being those that will move the teeth to desired relative positions such that the pre-attrition peak of the upper anterior tooth will be spaced from the upper archwire at a distance related to the distance of the mesial buccal cusp tip of an upper first bicuspid from the upper archwire.

32. A method of forming an orthodontic brace for positioning teeth of a patient, the method comprising the steps of:

digitally representing each of a plurality of individual teeth of the patient by a two dimensional contour in a vertical labial-facial plane, the contour including parameters of prominences of the tooth spaced in three dimensions over the surface thereof, the contour being generated by:

providing a three dimensional physical model of the patient's upper and lower jaws, the model including representations of individual teeth of the patient, including posterior teeth including molars and first and second bicuspids, and including anterior teeth including cuspids, laterals and centrals, and mechanically scanning individual teeth of the model with a mechanical probe and generating coordinate signals, including vertical coordinate data and horizontal, lingual-facial coordinate data of a plurality of prominences on the surface of the tooth;

digitally calculating with a processor, for each tooth, in response to the coordinate signals and in accordance with the coordinate data, the geometry of a bracket to be mounted at an attachment position located relative to the contour of the tooth, for connecting the teeth to an archwire so that, when brackets are attached to the attachment locations on a plurality of the teeth and connected to the archwire, forces will be exerted on the teeth to move the teeth to desired relative positions; and fabricating brackets in accordance with the calculated bracket geometry.

33. A method of forming an orthodontic brace for positioning teeth of a patient, the method comprising the steps of:

digitally representing individual teeth of the patient by a two-dimensional contour in a vertical labial-facial plane, the contour including parameters of prominences of a corresponding tooth, the contour being generated by:

providing a physical model of the patient's upper and lower jaws, the model including representations of individual teeth of the patient, including posterior teeth including molars and first and second bicuspids, and including anterior teeth including cuspids, laterals and centrals, mechanically scanning individual teeth of the model with a mechanical probe and generating coordinate signals, including vertical coordinate data and horizontal lingual-facial coordinate data thereby;

digitizing from the coordinate data, with respect to respective ones of the contours, a lingual tooth gum intersection point, a facial tooth gum intersection point, and:
    for posterior ones of the teeth, a mesial-buccal cusp tip, a mesial lingual cusp tip, and a mesial marginal ridge point, and
    for anterior ones of the teeth, a lingual incisal edge point and a facial incisal edge point;
digitally deriving with a processor, from the digitized parameters, additional parameters including:
    a crown long axis of individual teeth, the axes being:
        for posterior teeth, a line through a midpoint between parameters of tooth gum intersections and through a midpoint between parameters of cusp tip positions on the contour, and
        for anterior teeth, a line through a midpoint between parameters of tooth gum intersections and an incisal edge midpoint on the contour, and
    digitally representing orientations of the contour of each tooth in a respective vertical lingual-facial plane such that the crown long axis forms a long axis torque angle LAXTQ in accordance with a predefined criterium for the tooth, the LAXTQs being approximately equal to:
    for lower centrals, 63°,
    for lower laterals, 68°,
    for lower cuspids, 72°,
    for lower first bicuspids, 86°,
    for lower second bicuspids, 86°,
    for upper centrals, 73°,
    for upper laterals, 73°,
    for upper cuspids, 80°,
    for first bicuspids, 97°, and
    for second bicuspids, 100°;
selecting upper and lower archwires, each lying in an archwire plane and each having an arcuate shape;
for each of the upper and lower archwires:
    digitally defining the vertical position of the corresponding archwire plane relative to respective upper and lower molars wherein the plane is approximately horizontal and intersects each contour, as inclined, at two points spaced vertically from the parameter of the marginal ridge,
    for lower bicuspids, digitally defining the buccal cusp tips relative to the lower archwire plane a vertical distance that is derived from the distance between the buccal cusp tip and lower archwire plane for the lower molars,
    determining bracket attachment locations on the teeth at an intersection of the respective archwire plane with the contour;
digitally calculating, with a processor, for each tooth, the geometry of a bracket, including the position, depth and inclination of a slot therein, such that, when the bracket is mounted at the respective attachment location on a contour of the respective tooth, the slot lies in the archwire plane and has a depth extending:
    for molars, to a predetermined horizontal distance from attachment location, and defining thereby a horizontal reference distance from the marginal ridge for the upper molars, and a horizontal reference distance from the buccal cusp tips for the lower molars,
    for lower bicuspids, to a distance from the buccal cusp corresponding to the reference distance of the lower molars,
    for upper bicuspids, to a distance from the marginal ridge corresponding to the reference distance of the upper molars, and further defining thereby a horizontal reference distance from the buccal cusp tips for the upper bicuspids,
    for lower anteriors, to a distance from the incisal tip thereof corresponding to the reference distance for the lower molar,
    for upper anteriors, to a distance from the incisal tip thereof corresponding to the reference distance for the upper bicuspid; and
cutting slots in bracket blanks in accordance with the calculated geometries;
whereby, when the brackets are attached to the attachment locations relative to the contours of the respective teeth and the archwires are mounted in the slots of the brackets, a brace is formed that will exert forces on the teeth to move the teeth to desired positions at which the crown long axes thereof are at predetermined inclinations in the respective vertical lingual-facial planes, the mesial cusp tips of the molars are level, the mesial buccal cusps of the lower posterior teeth align vertically and horizontally with the marginal ridges of the corresponding upper posterior teeth, incisal edges of anterior teeth align by the prewear attrition points thereof.

* * * * *

UNITED STATES PATENT AND TRADEMARK OFFICE
CERTIFICATE OF CORRECTION

PATENT NO. : 5,395,238
DATED : March 7, 1995
INVENTOR(S) : Andreiko et al.

It is certified that error appears in the above-indentified patent and that said Letters Patent is hereby corrected as shown below:

Col. 2, line 44, after "U.S. Pat. No. 5,139,419" insert -- ,a method --.

Col. 14, line 47, "counter" should be -- contour --.

Signed and Sealed this

Twenty-ninth Day of August, 1995

*Attest:*

BRUCE LEHMAN

*Attesting Officer*    *Commissioner of Patents and Trademarks*